US010436869B2

(12) United States Patent
Ham

(10) Patent No.: US 10,436,869 B2
(45) Date of Patent: Oct. 8, 2019

(54) POSITIONING OF A MAGNETIC RESONANCE IMAGING ANTENNA WITHIN THE HOMOGENEOUS FIELD ZONE

(71) Applicant: KONINKLIJKE PHILIPS N.V., Eindhoven (NL)

(72) Inventor: Cornelis Leonardus Gerardus Ham, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 318 days.

(21) Appl. No.: 15/319,961

(22) PCT Filed: Jun. 25, 2015

(86) PCT No.: PCT/EP2015/064332
§ 371 (c)(1),
(2) Date: Dec. 19, 2016

(87) PCT Pub. No.: WO2015/197741
PCT Pub. Date: Dec. 30, 2015

(65) Prior Publication Data
US 2018/0210052 A1    Jul. 26, 2018

(30) Foreign Application Priority Data
Jun. 27, 2014   (EP) .................................... 14174749

(51) Int. Cl.
*G01R 33/54* (2006.01)
*A61B 5/055* (2006.01)
*G06T 11/00* (2006.01)

(52) U.S. Cl.
CPC .......... *G01R 33/543* (2013.01); *A61B 5/0555* (2013.01); *G06T 11/005* (2013.01)

(58) Field of Classification Search
None
See application file for complete search history.

(56) References Cited

U.S. PATENT DOCUMENTS 5,345,177 A * 9/1994 Sato .................... G01R 33/3854
                                                          324/318
7,218,106 B2   5/2007 Yasuhara et al.
(Continued)

OTHER PUBLICATIONS

Derbyshire et al "Dynamic Scan Plane Tracking Using MR Position Monitoring" Journal of Magnetic Resonance Imaing, Soc. for Magnetic Resonance Imaging. vol. 8, No. 4, Jul. 1, 1998 p. 924-932.
(Continued)

*Primary Examiner* — Brian T Gedeon

(57) ABSTRACT

The invention provides for a magnetic resonance imaging system (100) comprising: a magnet (104) for generating a main magnetic field with a homogeneous field zone (108); an antenna (124, 900, 1000) with an imaging zone (126) that has a fixed geometric relationship with portion (119) of a subject (118); a radio frequency system (114, 116, 124) for generating a radio frequency pulse (602); a magnetic gradient field system (110, 112); and a patient support (120, 122) for automatically moving the antenna and the portion of the subject from outside of the homogeneous field zone to within the homogeneous field zone along a movement axis. Machine executable instructions (180, 182, 184, 186, 188) cause a processor (136) controlling the magnetic resonance imaging system to: move the antenna and the portion from outside of the homogeneous field zone to within the homogeneous field zone along the movement axis; control (402) the radio frequency system to repeatedly generate a radio frequency pulse; control (404) the magnetic gradient field system to generate a gradient magnetic field during movement of the subject support only along the movement axis; control (406) the radio frequency system to repeatedly measure the radio frequency signal from the portion of the subject using the antenna; determine (408) a current location (128) of the antenna or of the imaging zone using the radio frequency signal; and control (410) the patient support to
(Continued)

decelerate and halt at a predetermined location (109) within the homogeneous field zone using the current location.

20 Claims, 10 Drawing Sheets

(56) References Cited

U.S. PATENT DOCUMENTS

| | | |
|---|---|---|
| 7,612,562 B2 | 11/2009 | Yasuhara |
| 8,035,380 B2 | 10/2011 | Kasugai |
| 2002/0021128 A1 | 2/2002 | Kuhara |
| 2005/0010544 A1 | 1/2005 | Sleat |
| 2006/0238192 A1 | 10/2006 | Ham |
| 2007/0225588 A1 | 9/2007 | Steckner |
| 2009/0285357 A1 | 11/2009 | Khamene et al. |
| 2010/0158338 A1 | 6/2010 | Harder |
| 2013/0279779 A1 | 10/2013 | Darrow |
| 2014/0055127 A1 | 2/2014 | Biber et al. |

OTHER PUBLICATIONS

Frahm et al "Rapid NMR Imaging Using Stimulated Echoes" Journal of Magnetic Resonance 65, p. 130-135 (1985).

* cited by examiner

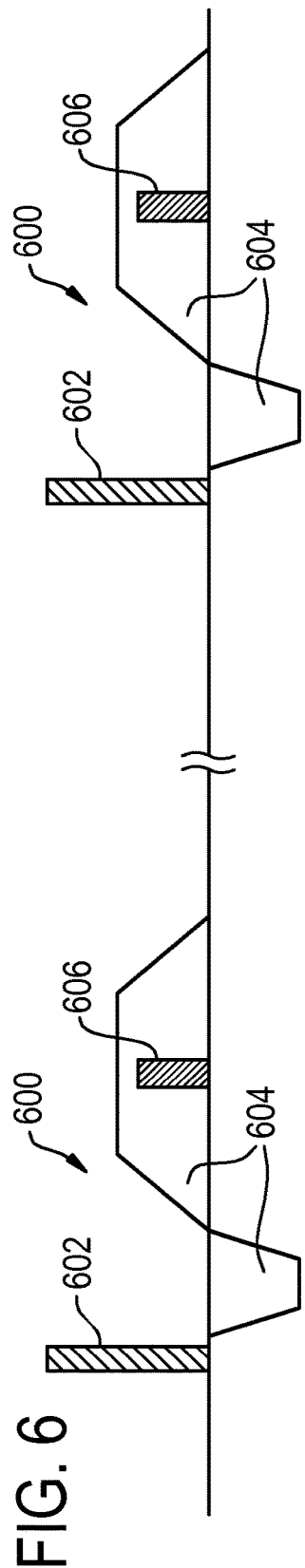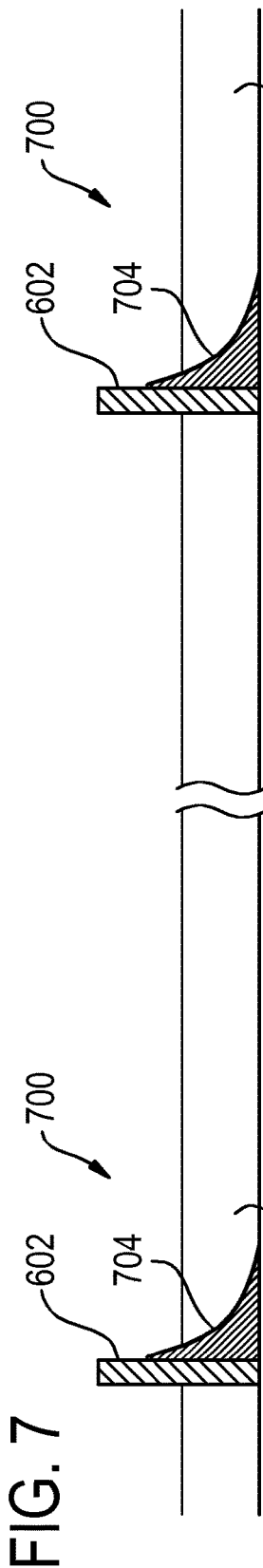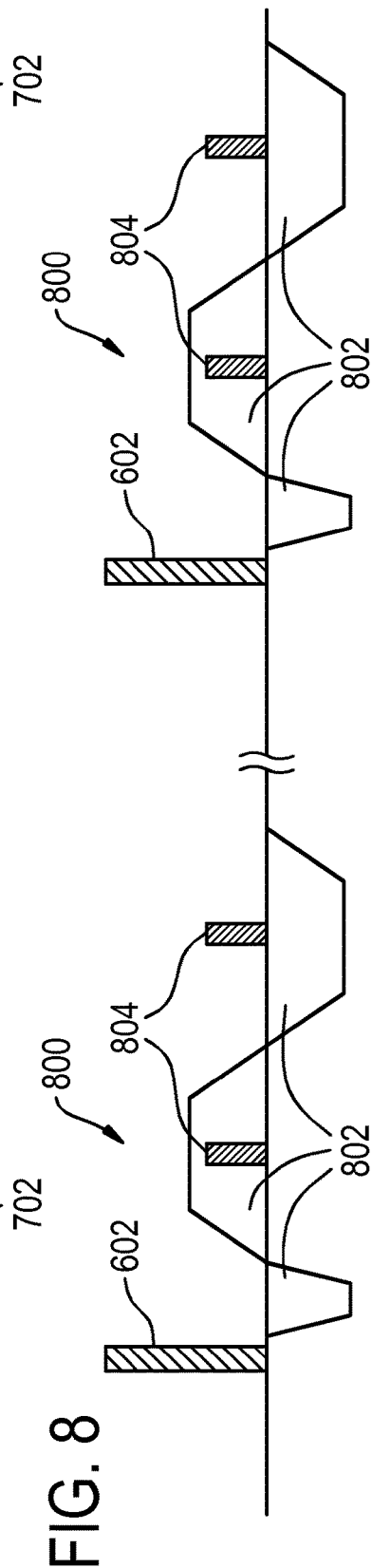

POSITIONING OF A MAGNETIC RESONANCE IMAGING ANTENNA WITHIN THE HOMOGENEOUS FIELD ZONE

CROSS REFERENCE TO RELATED APPLICATIONS

This application is a U.S. national phase application of International Application No. PCT/EP2015/064332 filed on Jun. 25, 2015, which claims the benefit of European Patent Application 14174749.3 filed on Jun. 27, 2014 and is incorporated herein by reference.

TECHNICAL FIELD

The invention relates to magnetic resonance imaging, in particular the invention relates to the positioning of an antenna within the homogeneous field zone of a magnetic resonance imaging magnet.

BACKGROUND OF THE INVENTION

A magnetic field is used in Magnetic Resonance Imaging to align the nuclear spins of atoms as part of the procedure for producing images within the body of a patient. This magnetic field is referred to as the BO field or main magnetic field. During an MRI scan, Radio Frequency (RF) pulses generated by a transmitter or amplifier and an antenna cause perturbations to the local magnetic field and can be used to manipulate the orientation of the nuclear spins relative to the BO field. Spatial encoding of the magnetic spins may be accomplished by using so called gradient coils, which are used to superimpose a magnetic field gradient upon the BO magnetic field. RF signals emitted by the nuclear spins are detected by a receiver coil, and these RF signals are used to construct the MRI images.

In order to perform magnetic resonance imaging, a superconducting magnet is typically used to generate the BO field. The BO field needs to have a large enough magnitude and uniformity to perform magnetic resonance imaging. The location where the magnet is able to generate a BO field of sufficient strength and uniformity is referred to herein as the homogeneous field zone.

Large body coils that are permanently mounted in the magnet are sometimes used to generate the RF pulses. In other cases smaller coils or antennas can be placed on or even attached to a subject. These smaller coils typically have a spatially dependent imaging zone where they are particularly sensitive for receiving a magnetic resonance signal and/or for transmitting a signal or RF pulse. To use such a smaller coil it should be positioned such that the imaging zone is within the homogeneous field zone of the magnet. Currently devices such as light visors are used to determine the location of the coil or antenna.

United States patent application US 20140055127 A1 discloses the use of wireless readable labels to determine the location of an antenna.

International patent application WO 2005/010544 A1 discloses, for a surface coil, applying gradient pulses in one or more directions followed by non-selective RF pulses. The location of the surface coil is then determined by calculating the center of gravity of the Fourier transformed response signals detected by the surface coil after applying non-selective RF pulses in each direction. The US-patent application US 2007/225588 mentions to employ a separate localisation device, notably based on fiducial markers, light reflecting markers, touch sensitive markers.

SUMMARY OF THE INVENTION

The invention provides for a magnetic resonance imaging system, a method of operating a magnetic resonance imaging system, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor.

'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a magnetic resonance imaging system for imaging a portion of a subject. The magnetic resonance imaging system comprises a magnet for generating a main magnetic field. The main magnetic field is also sometimes known as the BO. The main magnetic field has a homogeneous field zone. The homogeneous field zone as used herein encompasses a region where the magnetic field generated by the magnet is high and uniform enough for performing magnetic resonance imaging. For example the homogeneous field zone or homogeneous volume of a typical magnet is usually defined as the volume corresponding with 10 ppm peak-to-peak. The field outside this volume drops very quickly. This of course may depend upon the field order of the particular magnet design. Most typical modern magnets are twelfth order. This means that the field drops with the twelfth order of the z-position or along the axis of symmetry of the magnet. Because the field drops so rapidly outside of the homogeneous field zone the strength of the field drops very rapidly and it does not really matter if the main field is for example 1.5 T or 3.0 T. Outside of the homogeneous field zone the resonant frequency of protons or other nuclei is very quickly outside the frequency range of the radio-frequency system of the magnetic resonance imaging system.

The magnetic resonance imaging system further comprises an antenna with an imaging zone. There is a fixed geometric relationship between the antenna and the portion of the subject when the subject is mounted in the imaging zone. For example the antenna may be designed to receive a portion of the subject and clamp onto the subject. A typical example would be a head coil or a coil designed to be clamped onto a subject's ankle or wrist. The magnetic resonance imaging system further comprises a radio-frequency system for generating a radio-frequency pulse. The radio-frequency system is further operable for measuring a radio-frequency signal from the portion of the subject using the antenna. The radio-frequency system may generate the radio-frequency pulse in several different ways. In some examples the antenna may be used. In other examples an additional antenna or a body coil may be used to transmit the radio-frequency pulse. Full body coils are typically installed in the magnetic resonance imaging systems. In one example the body coil may be used to transmit the radio-frequency pulse and then the antenna with the imaging zone functions as a receive coil. In some other examples the antenna with the imaging zone is a transmit and receive coil or antenna. In this case the antenna with the imaging zone may be used to transmit and receive the radio-frequency pulse.

The magnetic resonance imaging system further comprises a magnetic gradient field system for generating a gradient magnetic field. Typically in magnetic resonance imaging systems there are three separate gradient coils that comprise a magnetic field gradient system. Very often they will generate three different orthogonal gradient fields. The magnetic resonance imaging system further comprises a patient support for automatically moving the antenna and the portion of the subject from outside of the homogeneous field zone to within the homogeneous field zone along a movement axis. For example hydraulics, pneumatics or mechanical system may be used to propel the patient support automatically to move the subject within a bore or central region of the magnet.

The magnetic resonance imaging system further comprises a memory contain machine-executable instructions. The magnetic resonance imaging system further comprises a processor for controlling the magnetic resonance imaging system. The processor also is designed or operable for executing the machine-executable instructions.

Execution of the machine-executable instructions causes the processor to control the patient support to move the antenna and the portion of the subject from outside the homogeneous field zone to within the homogeneous field zone along the movement axis. Execution of the instructions further causes the processor to control the radio-frequency system to repeatedly generate the radio-frequency pulse. An alternative wording that may be substituted into the claims and specification is that the patient support moves the imaging zone of the antenna from outside of the homogeneous field zone to within the homogeneous field zone along the movement axis.

Execution of the instructions further causes the processor to control the magnetic field gradient system to generate the gradient magnetic field during movement of the subject support only along the movement axis. Although the magnetic gradient field system may be designed to generate a magnetic field gradient in multiple directions, in this step the processor controls the magnetic gradient field system to generate the gradient magnetic field only in the direction along the movement axis. In some examples a gradient coil may be aligned such that the magnetic field gradient it generates is along the movement axis. In other examples more than one gradient coil may be used to generate the gradient magnetic field along the movement axis.

Execution of the machine-executable instructions further cause the processor to control the radio-frequency system to repeatedly measure the radio-frequency signal from the portion of the subject using the antenna.

Execution of the instructions further cause the processor to determine a current location of the antenna or of the imaging zone using the radio-frequency signal. When the antenna has been mounted or placed onto a subject it will generate a magnetic resonance signal in response to the radio-frequency pulse. The current location could for example be defined as the location of the maximum signal. For example, the location of the antenna or coil may be determined by calculating the center of gravity of the Fourier transformed response signals detected by the surface coil after generating non-selective RF pulses and applying a magnetic gradient field aligned with the motion axis. The location of the antenna along other directions could also be determined by generating non-selective RF pulses and applying a magnetic gradient field in each of the other directions. The location and strength of the Fourier transformed signal would be a function of the antenna. So in essence defining the current location could be referenced to the antenna or the location of the imaging zone. When one knows one of these, then the other is also known.

Execution of the instructions further cause the processor to control the patient support to decelerate and halt at a predetermined location within the homogeneous field zone using the current location.

As the patient support is moving the antenna and the portion of the subject into the homogeneous field zone the radio-frequency signal from the portion of the subject will begin to be received. For example when the imaging zone is only partially within the homogeneous field zone only a portion of the signal may be received and a false indication of where the current location is may be determined. For this reason as the patient support moves the antenna towards the homogeneous field zone the process is repeated over and over again so that the determination of the current location is detected properly. Once the imaging zone of the antenna is completely within the homogeneous field zone then the current location can be determined accurately and the patient support can be controlled to decelerate and halt at the predetermined location. This may be advantageous because it is not necessary to specify ahead of time the location of the antenna with the imaging zone. For instance the use of lights, lasers or other means to identify the position of the antenna before moving the subject into the magnet is not necessary. This may allow the performance of the magnetic resonance imaging protocol to be performed more rapidly. This may also eliminate the need of equipment to specify or locate the position of the antenna and/or the subject before the magnetic resonance imaging protocol begins.

In some embodiments the radio-frequency signal is recorded by the magnetic resonance imaging system as it is repeatedly measured.

In another embodiment the memory further contains magnetic resonance planning data descriptive of a magnetic resonance imaging scan geometry. Execution of the instructions further cause the processor to control the magnetic resonance imaging system to acquire imaging magnetic resonance data for the magnetic resonance imaging scan geometry. Execution of the instructions further causes the processor to reconstruct a magnetic resonance image from the imaging magnetic resonance data. In this example the subject is moved with the antenna into the imaging zone and imaging data is acquired automatically and the magnetic resonance image is also acquired automatically. The magnetic resonance planning data is descriptive of a magnetic imaging scan geometry and may be used by the processor to automatically execute a magnetic resonance imaging protocol.

In another embodiment the memory further contains scout scan pulse sequence instructions. The magnetic resonance planning data is descriptive of the magnetic resonance imaging scan geometry relative to anatomical landmarks of the subject. The memory further contains imaging pulse sequence instructions. Execution of the instructions further cause the processor to control the magnetic resonance imaging system to acquire scout magnetic resonance data using the scout scan pulse sequence instructions. Execution of the instructions further causes the processor to reconstruct the scout magnetic resonance data into a scout magnetic resonance image. Execution of the instructions further causes the processor to identify landmark location data by identifying the anatomical landmarks in the scout magnetic resonance image.

This embodiment may be beneficial because when the subject is moved into the magnet the system automatically performs scout scans and then identifies anatomical landmarks. These may be used to aid an operator in defining a magnetic resonance protocol or the landmark location data may be used as input to automatically perform a magnetic resonance imaging protocol. This may also include repositioning of the patient support.

In another embodiment execution of the instructions further cause the processor to modify the imaging pulse sequence instructions using the landmark location data and the magnetic resonance planning data to adjust the scan geometry. In this embodiment the landmark location data is used to adjust the imaging scan geometry such that a magnetic resonance imaging protocol is performed automatically. In this case the operator would put the subject on the subject support and attach the antenna to the subject. Then when the system starts the subject would be moved into the magnet automatically and the system would determine the current location. This would then cause the system to perform scout scans and then automatically a magnetic resonance imaging protocol by acquiring the magnetic imaging magnetic resonance data.

In another embodiment execution of the instructions further cause the processor to calculate a corrected movement of the patient support by using the landmark location data and the magnetic resonance planning data. Execution of the instructions further causes the processor to control the patient support to move by the determined distance. After a scout scan is performed and the landmark location data is identified the system then automatically corrects the position of the patient support. This may enable more rapid and accurate magnetic resonance imaging of the portion of the subject.

In another embodiment the gradient magnetic field along the movement axis is applied as a constant gradient magnetic field during movement of the subject support. In this embodiment the gradient field is turned on at a constant level in the direction of the movement axis and is left on constantly. This has the advantage that it produces less noise. The coils for making the gradient magnetic field are within a very high magnetic field. When a current is run through them as a pulse it typically makes a clunking or clanging sound inside of the magnetic resonance imaging system. By applying the gradient field as a constant the gradient coil will make a noise when the gradient coil is first turned on and then remain in its position. This may make the experience more pleasant for a subject being moved into the magnet instead of hearing a repetition of clanging sounds or sledgehammer like sounds, the process will be silent.

In another embodiment execution of the instructions further causes the processor to control the magnetic gradient field system to increase the gradient magnetic field at a predetermined rate as the current location approaches the predetermined location. For example the magnetic gradient field may be increased a slow rate such that acoustic noise is not generated. For a particular measurement of the radio frequency signal the rate of increase of the gradient magnetic field may be low enough that it is essentially or behaves like a constant gradient field for that particular measurement.

In another embodiment the radio-frequency signal is a free induction decay that starts after the generation of the radio-frequency pulse.

In another embodiment the gradient magnetic field along the movement axis is repeatedly generated as a gradient magnetic field pulse during movement of the subject support. For example the gradient may be in the direction of the movement the gradient amplitude may for example be between 0.5 mT/m and 40 mT/m.

In another embodiment the gradient magnetic field pulse is generated after the radio-frequency pulse is generated and before the measurement of the radio-frequency signal. As an alternative one can also use multiple echoes that are generated using bipolar gradient switching. This other alternative may have the benefit of eliminating influence from static field gradients.

In another embodiment the current location indicates a location of the imaging zone. For example the current location may be the portion of the imaging zone which gives the greatest signal.

In another embodiment the radio-frequency pulse is a non-selective pulse. For example the radio-frequency pulse may be a pulse of a single frequency that is modulated by a square wave. For a short RF pulse, this may include a low number of oscillations so that there is a large bandwidth that is excited by the non-selective pulse.

In another embodiment execution of the instructions cause the processor to generate a radio-frequency pulse at an increased rate and/or an increase gradient magnetic field as the current location approaches the predetermined location. Increasing the rate at which the radio-frequency pulses are generated may give a calculation of the current location more often. This may assist in more accurately matching the current location to the predetermined location. Using an increased magnetic gradient field may have the effect of allowing the more accurate determination of the current location. As the current location approaches the predetermined location it may be beneficial to have a more accurate determination of the current location. For example if a constant gradient field is used the gradient magnetic field may be increased at a slow or controlled rate so that there is no noise generated.

In another aspect the invention provides for a method of operating the magnetic resonance imaging system. The magnetic resonance imaging system may be used for imaging a portion of a subject. The magnetic resonance imaging system comprises a magnetic for generating a main magnetic field. The main magnetic field has a homogeneous field zone. The magnetic resonance imaging system further comprises an antenna with an imaging zone. There is a fixed geometric relationship between the antenna and the portion of the subject when the subject is mounted in the imaging zone. The magnetic resonance imaging system further comprises a radio-frequency system for generating a radio-frequency pulse. The radio-frequency system is further operable for measuring a radio-frequency signal from the portion of the subject using the antenna. The magnetic resonance imaging system further comprises a magnetic gradient field system for generating a gradient magnetic field. The magnetic resonance imaging system further comprises a patient support for automatically moving the antenna and a portion of the subject from outside of the homogeneous field zone to within the homogeneous field zone along a movement axis.

The method comprises the step of controlling the patient support to move the antenna and the portion of the subject from outside of the homogeneous field zone to within the homogeneous field zone along a movement axis. The method further comprises the step of controlling the radio-frequency system to repeatedly generate the radio-frequency pulse. The method further comprises the step of controlling magnetic gradient field system to generate the gradient magnetic field during movement of the subject support only along the movement axis. The method further comprises the step of controlling the radio-frequency system to repeatedly measure the radio-frequency signal from the portion of the subject during using the antenna. The method further comprises the step of determining a current location of the antenna or of the imaging zone using the radio-frequency signal. The method further comprises the step of controlling the patient support to decelerate and halt at a predetermined location within the homogeneous field zone using the current location.

In another aspect the invention provides for a computer program product comprising machine-executable instructions for execution by a processor controlling the magnetic resonance imaging system. The magnetic resonance imaging system may be used for imaging a portion of a subject. The magnetic resonance imaging system comprises a magnet for generating a main magnetic field. The main magnetic field has a homogeneous field zone. The magnetic resonance imaging system further comprises an antenna with an imaging zone. There is a fixed geometric relationship between the antenna and the portion of the subject when the subject is mounted in the imaging zone or in the antenna. The magnetic resonance imaging system further comprises a radio-frequency system for generating a radio-frequency pulse. The radio-frequency system is further operable for measuring a radio-frequency signal from the portion of the subject using the antenna. The magnetic resonance imaging system further comprises a magnetic gradient field system for generating a gradient magnetic field.

The magnetic resonance imaging system further comprises a patient support for automatically moving the antenna and a portion of the subject from outside of the homogeneous field zone to within the homogeneous field zone along the movement axis. Execution of the machine-executable instructions causes the processor to control the patient support to move the antenna and a portion of the subject from outside of the homogeneous field zone to within the homogeneous field zone along the movement axis. Execution of the instructions further causes the processor to control the radio-frequency system to repeatedly generate the radio-frequency pulse. Execution of the instructions further cause the processor to control the magnetic gradient field system to generate the gradient magnetic field during movement of the subject support only along the movement axis. Execution of the instructions further causes the processor to control the radio-frequency system to repeatedly measure the radio-frequency signal from the portion of the subject using the antenna. Execution of the instructions further cause the processor to determine a current location of the antenna or of the imaging zone using the radio-frequency signal. Execution of the instructions further cause the processor to control the patient support to decelerate and halt at a predetermined location within the homogeneous field zone using the current location.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIG. 6 illustrates an example of a pulse sequence;

FIG. 7 illustrates a further example of a pulse sequence;

FIG. 8 illustrates a further example of a pulse sequence;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
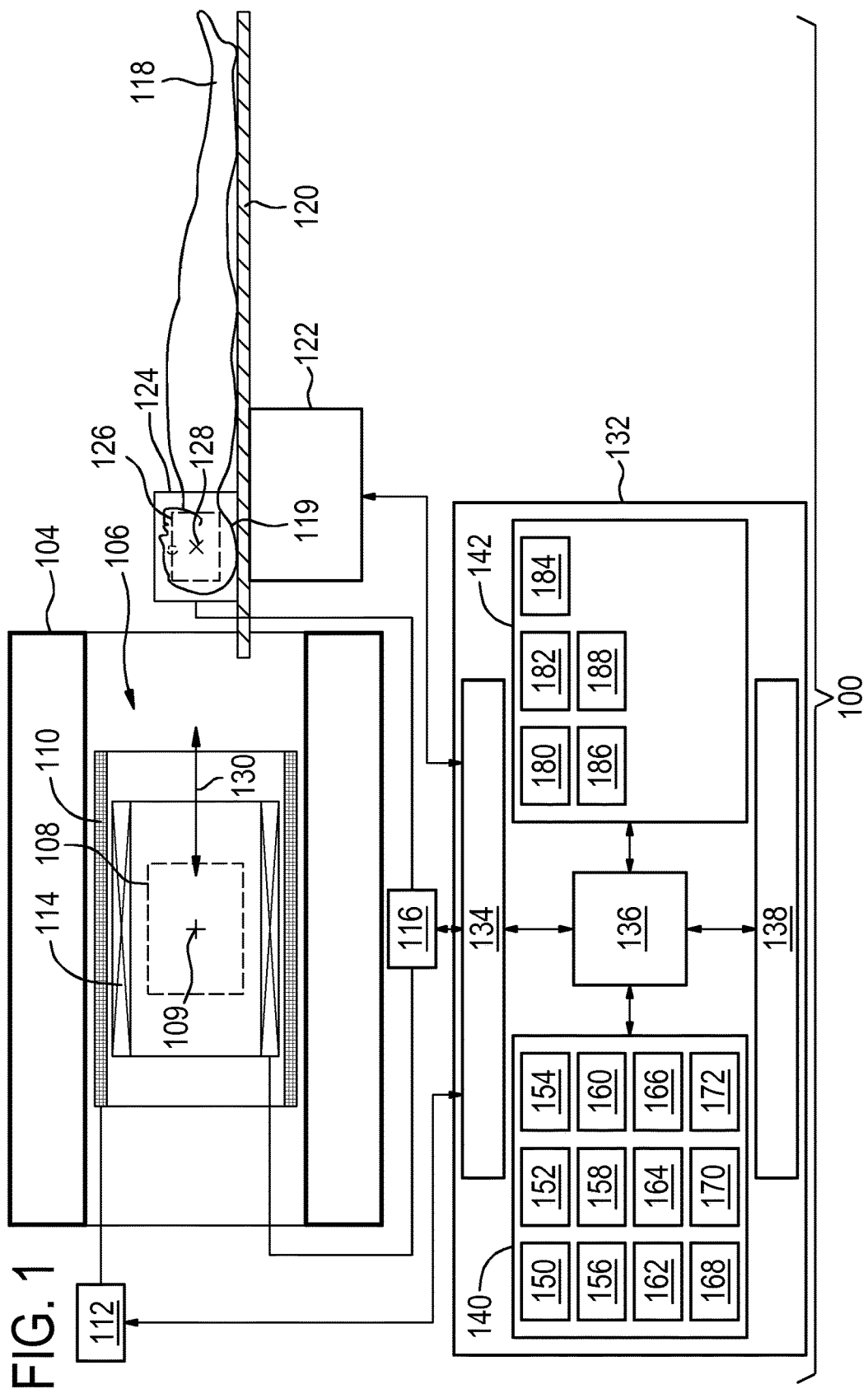
FIG. 1 illustrates an example of a magnetic resonance imaging system.

FIG. 1 shows an example of a magnetic resonance imaging system 100. FIG. 1 illustrates an example of a medical instrument 100. The medical instrument 100 comprises magnetic resonance imaging system 102 with a magnet 104. The magnet 104 is a superconducting cylindrical type magnet with a bore 106 through it. The magnet may also be a permanent magnet or a resistive magnet. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is a homogeneous field zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the homogeneous field zone 108 of the magnet 104.

At the center of the homogeneous field zone 108 is marked a center 109 of the homogeneous field zone.

The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

There is a subject 118 shown as reposing on a subject support 120. The subject support 120 is resting upon a mechanism 122 which is able to move the subject support 120 in and out of the bore of the magnet 104.

A body coil 114 is shown as being optionally connected to a radio-frequency transceiver 116. The body coil is within the bore 106 of the magnet. In this example the subject 118 is shown as having a head coil (sometime referred to as "coil") 124 or antenna 124, which may be a radio frequency antenna. The antenna 124 is connected to the radio-frequency transceiver 116. The antenna 124 has an imaging zone 126. The imaging zone 126 is a region where the antenna 124 can be used to receive magnetic resonance data. In some examples the antenna 124 can also be used to transmit the radio-frequency pulse. The point 128 is the center of the imaging zone 126. When the mechanism 122 moves the subject support 120 the subject 118 and the antenna 124 are moved along the movement axis 130. In this example a movement axis 130 coincides with the z-axis of the magnet 104.

The body coil 114 may be used for manipulating the orientations of magnetic spins within the homogeneous field zone 108 and in some examples for receiving radio transmissions from spins also within the homogeneous field zone 108. Body coil 114 of the antenna 124 may contain multiple coil elements. The radio frequency antenna 124 may also be referred to as a channel or antenna.

The body coil 114 and the antenna 124 are both shown as being connected to the radio frequency transceiver 116. In some examples the body coil 114 is used for transmitting a radio-frequency pulse and the antenna 124 is used for receiving magnetic resonance data from the imaging zone 126. In other examples the body coil 114 may not even be present. In this case the antenna 124 is both a transmit and receive coil. In this case the antenna 124 may be used for transmitting the radio-frequency pulse and also receiving the radio-frequency signal. In this example the portion of the subject 118 is the subject's head.

The magnetic field gradient coil power supply 112, the radio frequency transceiver 116, and the mechanism 122 are shown as being connected to a hardware interface 134 of the computer system 132. The computer system 132 further comprises a processor 136. The processor 136 is connected to the hardware interface 134, a user interface 138, computer storage 140, and computer memory 142.

The computer storage 140 is shown as containing a location pulse sequence 150. The location pulse sequence used by the processor 136 to control the radio-frequency system to repeatedly generate the radio-frequency pulse, to control the magnetic gradient field system to generate the gradient magnetic field during movement of the subject support only along the movement axis, and also to control the radio-frequency system to repeatedly measure the radio-frequency signal from the portion of the subject using the antenna 124. The computer storage 140 is shown as further containing a radio-frequency signal 152 that was measured after executing the location pulse sequence 150. The computer storage 140 is further shown as containing a current location of the coil 154 which is determined by examining the radio-frequency signal 152. For example the radio-frequency signal may give a radio-frequency pulse which has a maximum indicated somewhere along the movement axis 130. The computer storage 140 is shown as containing a location of a predetermined location 156. For example the predetermined location 156 may be the center 109 or may be a value offset some location from the center 109.

The computer storage 140 is shown as optionally containing magnetic resonance planning data 158. The magnetic resonance planning data 158 defines a scan geometry which may be used for acquiring the magnetic resonance image. The computer storage 140 is shown as further containing a magnetic resonance imaging pulse sequence 160 that may be used for acquiring magnetic resonance data in accordance with the magnetic resonance planning data 158. The computer storage 140 is further shown as containing magnetic resonance data 162 that was acquired using the magnetic resonance imaging pulse sequence 160. The computer storage 140 is further shown as containing a magnetic resonance image 164 that was reconstructed from the magnetic resonance data 162.

The computer storage 140 is further shown as containing a scout scan pulse sequence 166 that is useful for taking a scout scan once the current location has been moved to the predetermined location. The computer storage 140 shows the scout scan magnetic resonance data 168 acquired using the scout scan pulse sequence 166. The computer storage 140 is further shown as containing a scout magnetic resonance image 170 that was reconstructed from the scout scan magnetic resonance data 168. The computer storage 140 is further shown as containing anatomical landmark locations 172 that were determined by performing a registration on the scout magnetic resonance image 170. One or more of the features numbered 158-172 may or may not be present in different examples. For example in some examples the software may only move the subject and the antenna 124 to the predetermined location. In other examples the magnetic resonance image and/or the scout scan are performed automatically.

The computer memory 142 is shown as containing a control module 180. The control module 180 contains computer-executable code which enables the processor 136 to control the magnetic resonance imaging system 100. For example the control module 180 may enable the processor 136 to use various pulse sequences 150, 160, 166 to acquire magnetic resonance data of various types (e.g., the radio-frequency signal 152, magnetic resonance data 162, and scan scout resonance data 168. The computer memory 142 is further shown as containing a magnetic resonance data processing module 182. For instance the magnetic resonance data processing module 182 may enable the processor 136 to examine the radio-frequency signal 152 to determine the current location of the coil 154. For instance the magnetic resonance data processing module 182 may calculate a spatially-dependent signal along the movement axis 130. The computer memory 142 is further shown as containing an image reconstruction module 184.

The image reconstruction module 184 may be used for constructing magnetic resonance data 162, 168 into a magnetic resonance image 164, and scout magnetic resonance data 170. The computer memory 142 is further shown as containing an image registration module 186. The image registration module 186 may contain computer-executable code which enables the processor 136 to perform a registration on the scout magnetic resonance image 170 to determine the anatomical landmark locations 172. The computer memory 142 may further contain a magnetic resonance planning data adjustment module 188. The magnetic resonance planning data adjustment module 188 may contain code which enables the processor 136 to adjust the magnetic resonance imaging pulse sequence 160 and/or the position of the patient support using the magnetic resonance planning data 158 and the anatomical landmark locations 172. The location of the subject and/or the location where magnetic resonance imaging data is acquired can be adjusted.

The contents of the computer storage 140 and the computer memory 142 may be exchanged or duplicated with each other.

Figure 2:
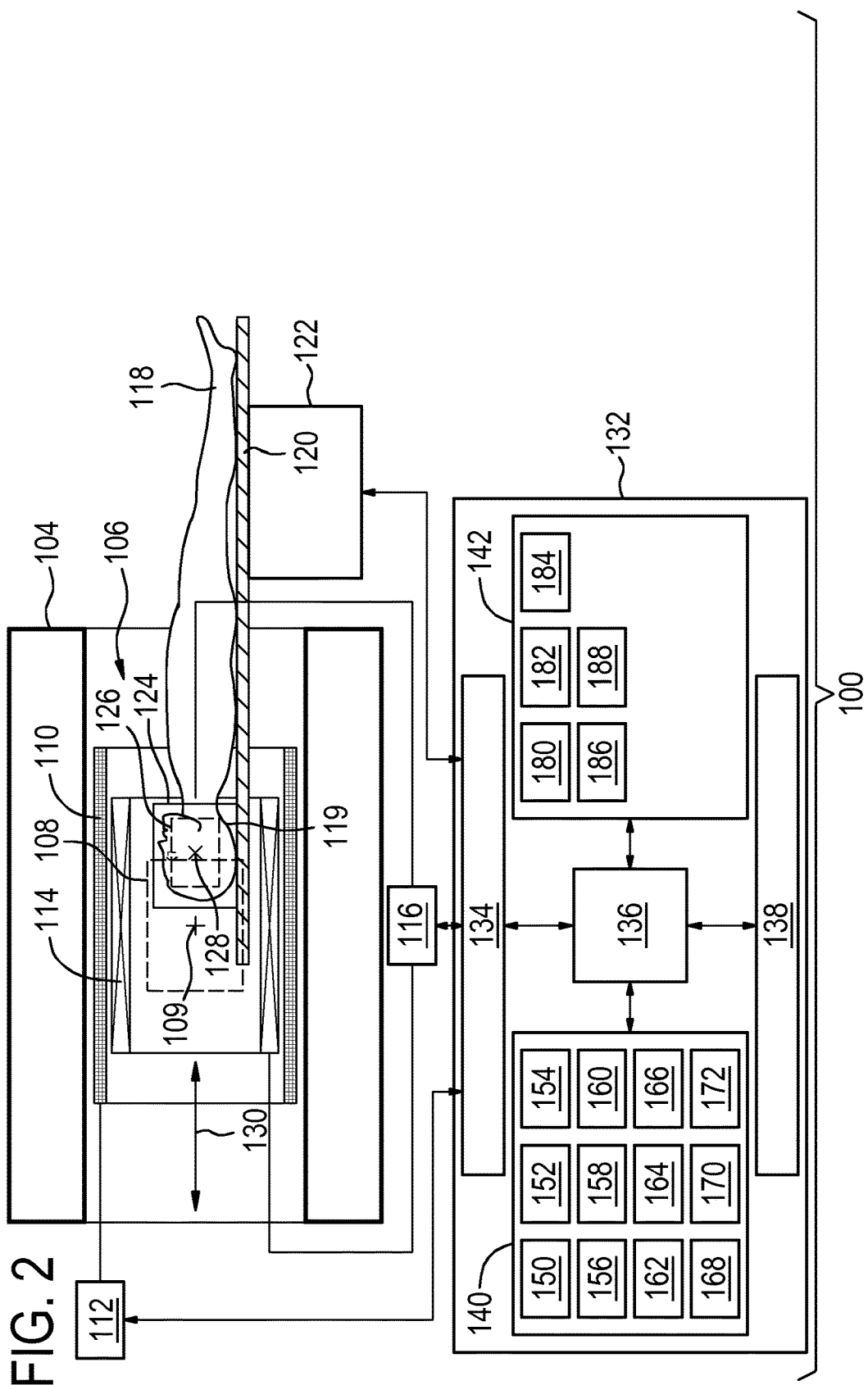
FIG. 2 shows the magnetic resonance imaging system of FIG. 1 after the imaging zone has been partially moved into the homogeneous field zone.
Figure 3:
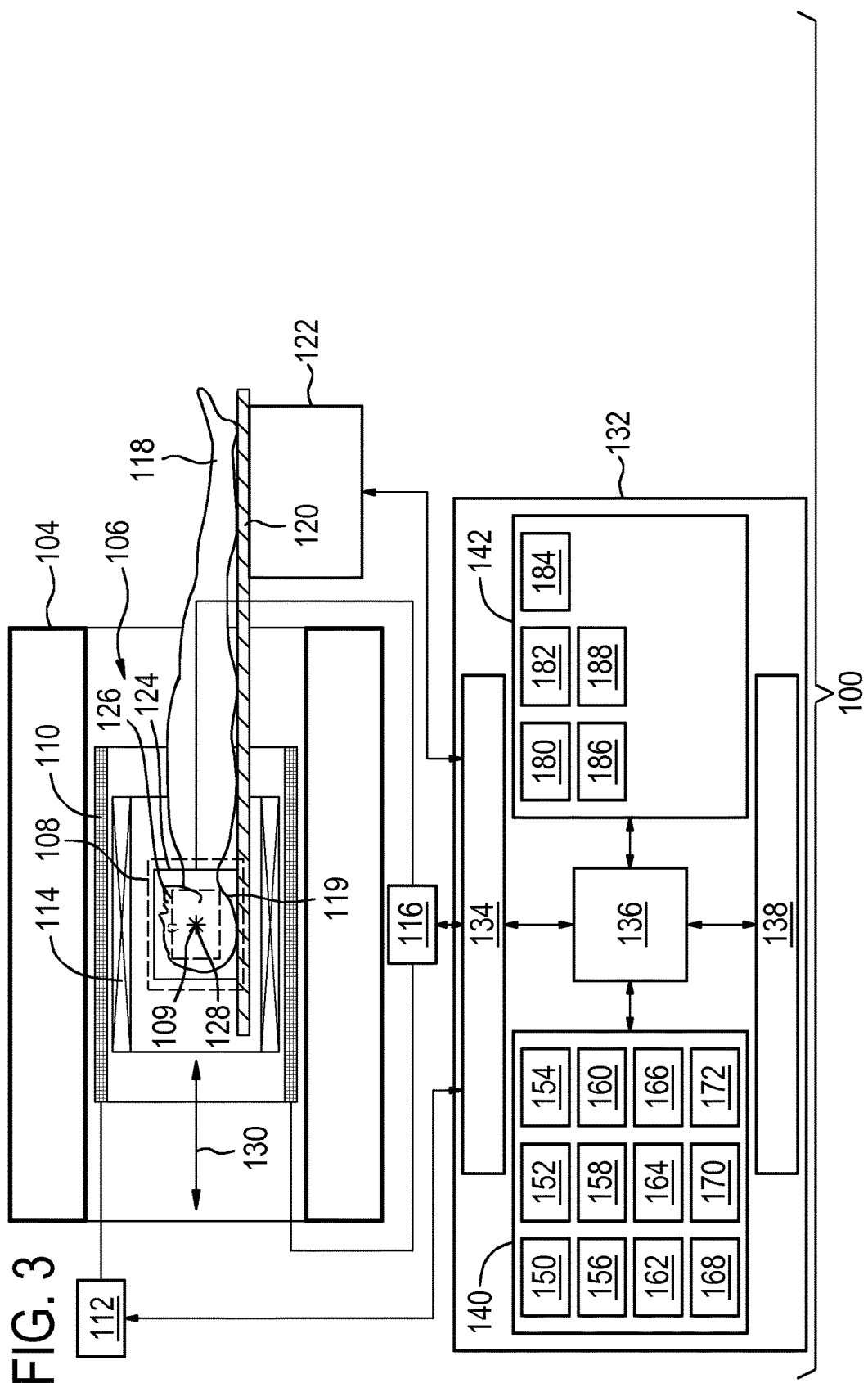
FIG. 3 shows the magnetic resonance imaging system of FIG. 1 after the imaging zone has been moved into the homogeneous field zone.

FIG. 1 shows the subject and the antenna 124 outside of the bore of the magnet 104. FIGS. 2 and 3 show the subject and the coil 124 being moved into the homogeneous field zone 108 by the subject support 120 and the mechanism 122.

In FIG. 2 the coil 124 has been partially moved into the homogeneous field zone 108. In this example the center of the imaging zone 126 is still outside of the homogeneous field zone 108. In this case the magnetic field drops off rapidly outside of the homogeneous field zone 108. Likely only a signal from a small portion of the imaging zone 126 is received. The maximum will then therefore not be at the center of the imaging zone 126. A signal from a large portion of the imaging zone 126 will not be at the correct frequency to be received by the antenna 124 and the radio frequency transceiver 116. When the subject 118 is in this position the current location of the coil 154 will likely be incorrect. In FIG. 1 the subject 118 is completely out of the magnet 104. The magnetic resonance imaging system 100 will not be able to determine the current location of the coil 154. As the coil 124 has its imaging zone 126 moved into the homogeneous field zone 108 the current location of the coil 154 will then begin to be determined accurately. For this reason the magnetic resonance imaging system 100 repeatedly executes the location pulse sequence 150.

FIG. 3 shows the same magnetic resonance imaging system as in FIGS. 1 and 2. In this case the imaging zone 126 has been moved completely into the homogeneous field zone 108. In this case the center of the imaging zone 126 has been moved so that it coincides with the center 109 of the homogeneous field zone. For example the center of the imaging zone 126 may be the location in some embodiments. The center 109 of the homogeneous field zone may be the determined location in some examples. In other examples the current location may be an offset of the point 128. The predetermined location may in some examples be an offset from the center 109. In this case center 109 and point 128 have been made to coincide. The center of the imaging zone 126 has been moved to the center of the homogeneous field zone 108 automatically. As the point 128 approaches the center 109 the system may have increased the strength of the gradient field in the direction of the movement axis 130 and/or the pulse sequence 150 may have been executed more frequently.

Figure 4:
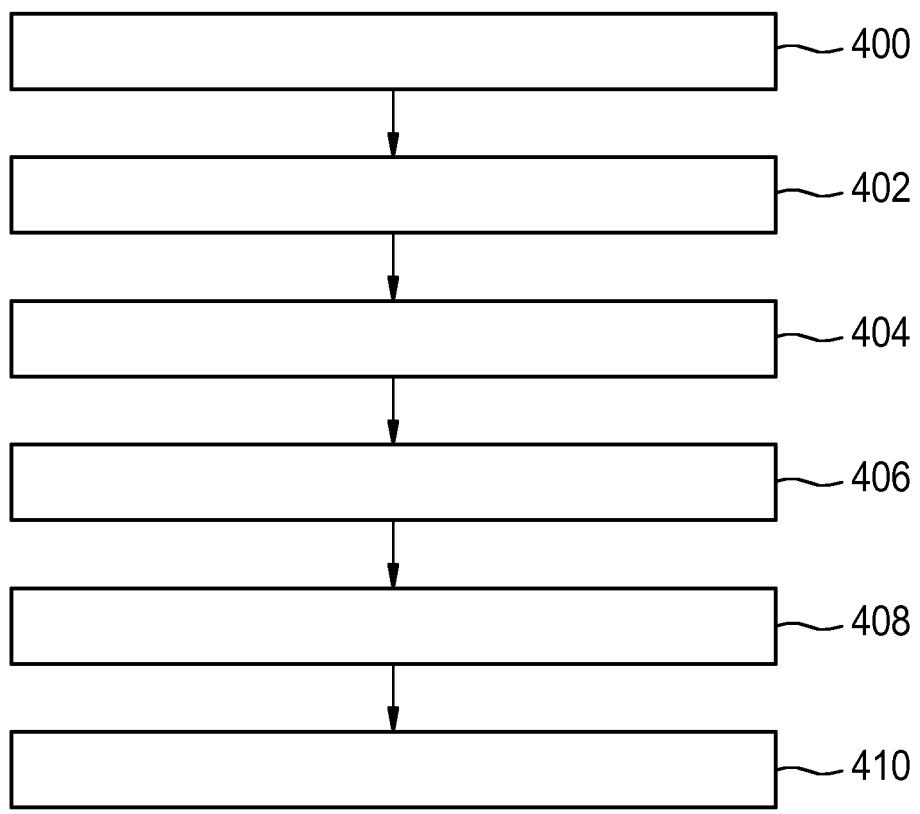
FIG. 4 shows a flow chart which illustrates a method of operating the magnetic resonance imaging system of FIG. 1.

FIG. 4 shows a flowchart which illustrates a method of operating the magnetic resonance imaging system 100 shown in FIGS. 1, 2 and 3. First in step 400 the patient support is controlled such that it moves the antenna 124 and the portion 119 of the subject 118 from outside of the homogeneous field zone 108 to within the homogeneous field zone 108 along the movement axis 130. This step could also be interpreted as moving the imaging zone 126 to within the homogeneous field zone 108. This step is shown in FIGS. 1-3. Next in step 402 the radio-frequency system is controlled to repeatedly generate the radio-frequency pulse. Next in step 404 the magnetic gradient field coils 110, and magnetic gradient field coil power supply 112 are controlled to generate the gradient magnetic field during movement of the subject support 120 only along the movement axis 130. Next in step 406 the radio-frequency system comprising the radio-frequency transceiver 116, the magnetic gradient field coil power supply 112, and the antenna 124 to repeatedly measure the radio-frequency signal 152 from the portion 119 of the subject 118 using the antenna 124. Next in step 408 a current location is determined using the radio-frequency signal 152. Finally in step 410 the subject support 120 is controlled to decelerate and halt at the center 109 and a predetermined location 156 within the homogeneous field zone 108 using the current location.

In examples, the targeted anatomy is brought to the isocenter or predetermined location in a two-step approach: 1. Course positioning in such a way that a survey scan can be performed on which the operator can plan the following diagnostic scans or that a SmartExam can be performed where the system recognizes a set of landmarks based on which the system proposes the planning of the diagnostic scans. A SmartExam as used herein encompasses an automated or partially automated magnetic resonance imaging protocol.

2. Fine positioning (if needed), based on the planning information from the survey or a SmartExam.

The idea is to provide a method for the course positioning, based on the MR response from some coil element(s). This will be explained in the following steps:

1. A receive coil is positioned at the patient's targeted anatomy (head, knee, wrist, breast, cardiac, etc.).

2. The Magnetic Resonance (MR) signal from this coil (or only a few coil elements from this coil) is used for this method. For instance use the neck elements of the head-neck coil in case the targeted anatomy is the C-spine or cervical spine. For the knee all coil elements can contribute.

3. While moving into the magnet, RF excitation pulses are given. This can be a non-selective pulse with a low flip angle.

4. The MR signal is detected with the receive coil. Most of the signal that is received, comes from the 'sweet spot' of the coil. The 'sweet spot' of the coil (or coil elements) corresponds with the targeted anatomy. After moving this sweet spot to the isocenter, the targeted anatomy is in or close to the isocenter.

5. A sufficient amount of MR signal will be received when the coil (element(s)) is in a reasonably homogeneous field. In other words, MR reception starts when the coil (elements) enters the imaging volume.

6. During reception a z-gradient is applied. The FFT of the MR signal gives a frequency distribution, where the 'sweet spot' of the coil gives the highest peak. The peak corresponds with the z-position of the coil.

7. The acquisition has two variants:
   a. The z-gradient can be kept at a constant value (no switching). The MR signal is a FID. In this case the scanner makes no acoustical noise.
   b. Alternatively the z-gradient is switched to generate an echo. The slew rate and the gradient amplitude can be chosen at a low value in order to keep the acoustic noise at a low level.

8. In this way the scanner knows the position every, say, 50 ms. The system will automatically decelerate when the coil is approaching the isocenter and finally stop when the coil is in the isocenter.

9. For higher position accuracy the gradient amplitude can be increased when approaching the isocenter.

A Survey/SmartExam scan may be started, when the coil (element(s)), or actually its sweet spot, is in the isocenter.

Figure 5:
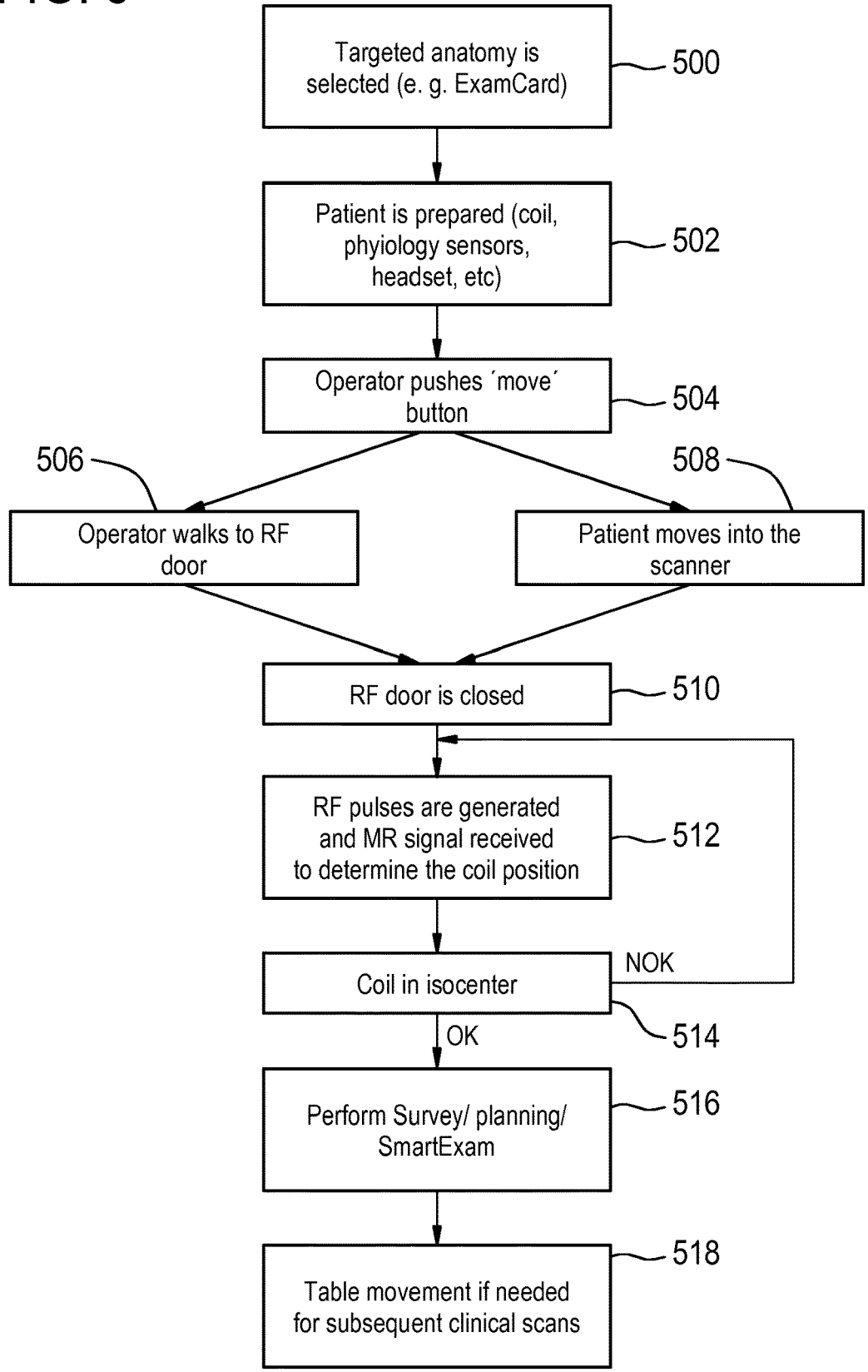
FIG. 5 shows a flow chart which illustrates a further method of operating a magnetic resonance imaging system.

FIG. 5 shows a flowchart which illustrates a workflow that can be accomplished using the magnetic resonance imaging system 100 of FIG. 1. First in step 500 a target anatomy is selected. For example a magnetic resonance planning data or exam card may be selected. Next in step 502 the patient is prepared for example the coil, physiology sensors, headset and other components may be put on the subject. The patient may also be placed on the subject support 120. Next in step 504 the operator pushes a move or start button. This may also be a control on the user interface 138. Next steps 506 and 508 are performed at the same time. The operator walks to the RF door of the RF cage and the patient is moved into the scanner 508 automatically as it is shown in FIGS. 1-3. Next in step 510 the operator has left the room and the RF door is closed. Next in step 512 RF pulses are generated and magnetic resonance signals are received to determine the coil position. Step 514 is a decision box, is the coil 124 located in the center 109. If it is not then the step returns to step 512 and the RF pulses are generated again. Once the coil is in the center 109 the method then goes to step 516 where a survey or planning scan is performed according for example to a smart exam protocol. Next in step 518 subject support 120 may be moved again if there is a need for subsequent clinical scans.

FIG. 6 illustrates a switched gradient pulse 600 that may be used to determine the location of the coil. In the pulse sequence first there is a transmit pulse or RF pulse 602. Next a switched z-gradient 604 is applied. The switched z-gradient 604 is assumed to be applied in the movement axis. The RF pulse 602 may be a non-selective RF pulse. The switched z-gradient 604 refocuses the signal that is received.

A scan technique which does not produce acoustic noise is highly preferred by the patient. This is the case for the method with the constant gradient.

The radio frequency pulses used herein may in some examples have a duration of 50 µs.

In order to avoid stimulated echoes, spoiler gradients can be used in x- and/or y-gradient (or gradients orthogonal to the motion direction). This enables a shorter repetition time.

The above mentioned scan techniques can have many variants (Spin echo scan, use of slice-selective pulses, etc. . . . ). The most important part of all variants is the readout with z-gradient to obtain the z-position of the sweet spot.

FIG. 7 shows a further example of the pulse sequence 700 that may be used to determine the current location of the coil. For example there is a constant gradient 702 that is applied. The gradient can be seen as always being on. The constant gradient 702 is applied in the motion direction. For example if the motion direction is along the z-axis then the constant gradient 702 is a constant z-gradient. In this example the transmit or RF pulse 602 is applied and then as soon as this pulse is over a free induction decay 704 is received as the radio-frequency signal. The free induction decay 704 will contain different frequency components which indicate a location along the movement axis.

FIG. 8 shows an example of a pulse sequence 800 that can be used to determine the current location using a switched gradient with multiple echoes. In this example first a radio-frequency pulse 602 is applied. Next a switched gradient 802 is applied. For example the gradient may again be applied in the direction of the movement direction. This switched gradient 802 causes multiple echoes 804 to be received. The echoes 804 are the radio-frequency signals that are used to determine the current location.

Figure 9:
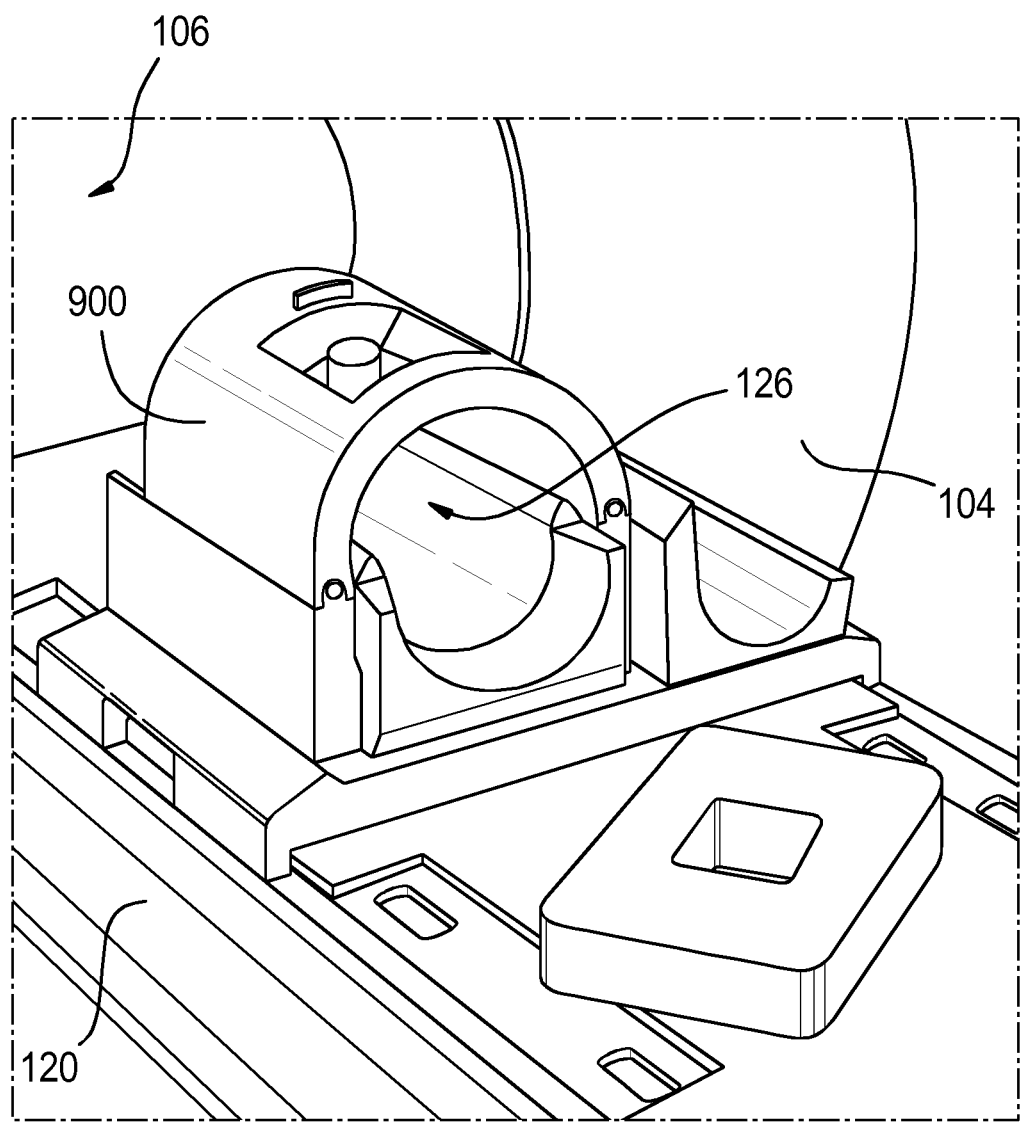
FIG. 9 illustrates an example of a foot and ankle coil.
Figure 10:
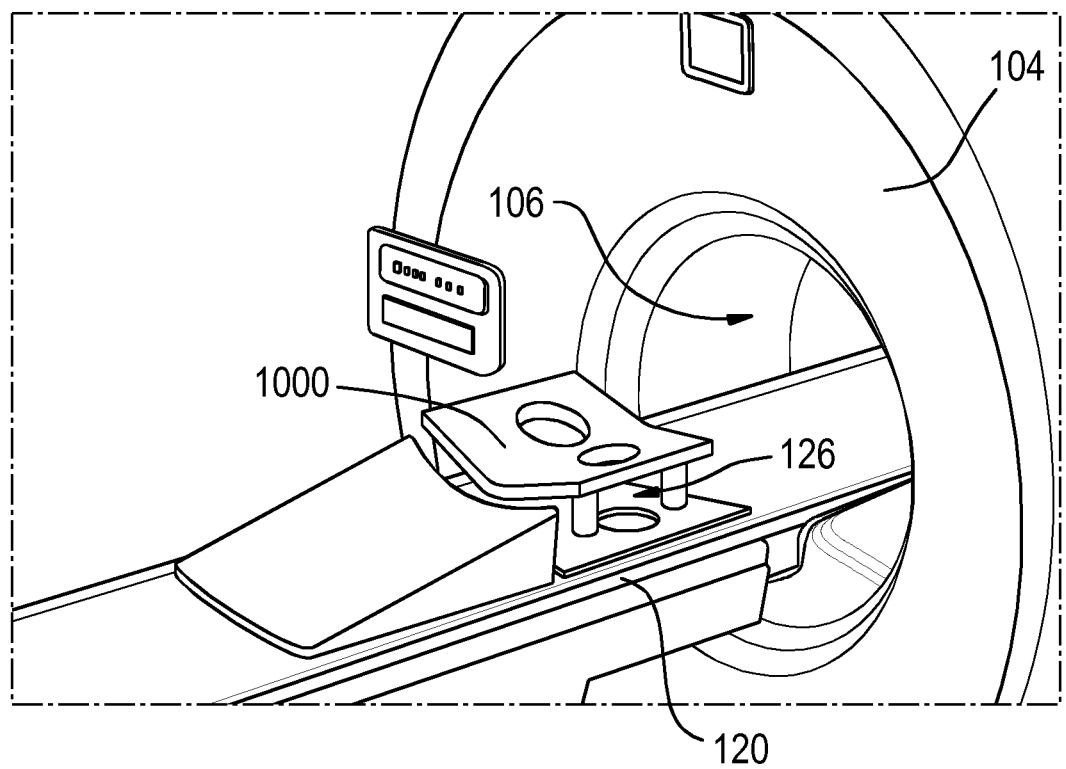
FIG. 10 illustrates an example of a breast coil with two regions for receiving breasts.
Figure 11:
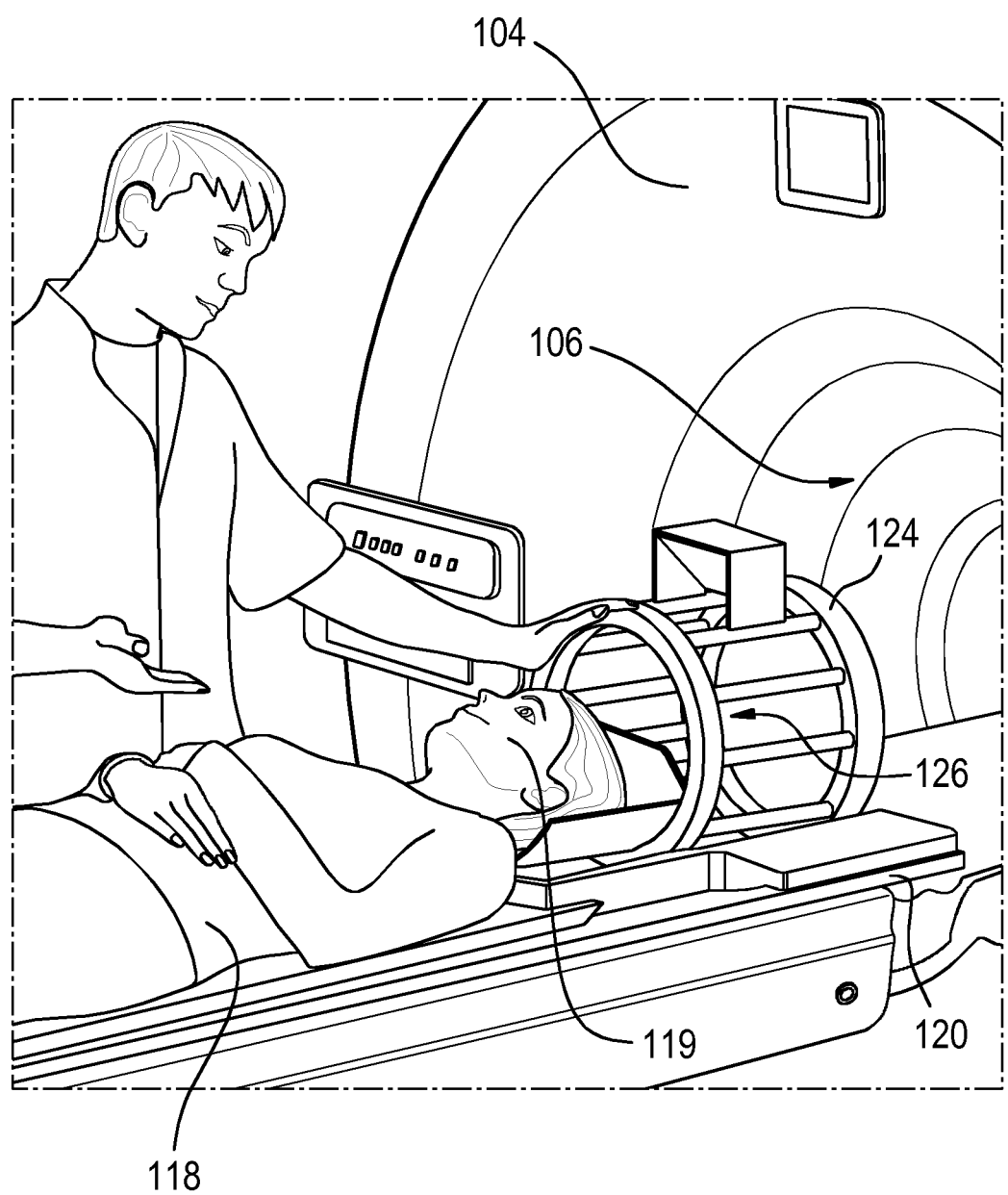
FIG. 11 illustrates an example of a subject having her head being placed into a head coil.

FIGS. 9, 10, and 11 show different examples of antennas within the imaging zone that have a fixed geometric relationship between the antenna and a portion of the subject.

FIG. 9 shows an example of a foot and ankle coil 900. The foot or ankle can be placed within the foot and ankle coil 900.

FIG. 10 shows an example of a breast coil 1000 with two regions for receiving breasts.

FIG. 11 shows an example of a patient having her head being placed into a head coil 124.

Figure 13:
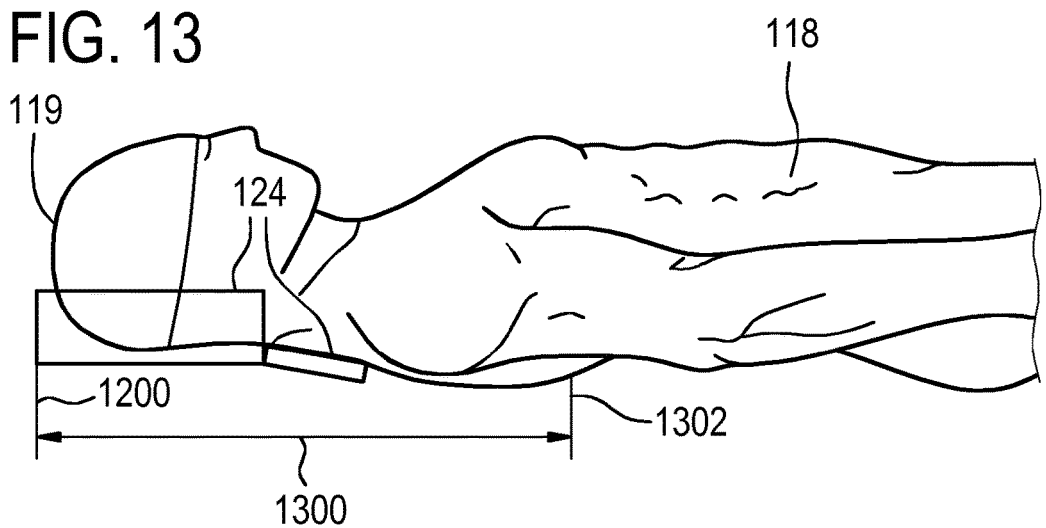
FIG. 13 shows an example where the coil location is simply used for positioning the subject.
Figure 14:
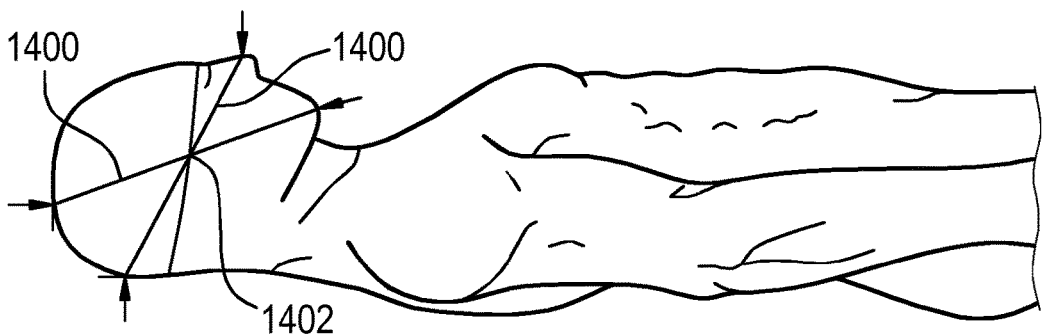
FIG. 14 illustrates several scout scans and their use to determine a head center location.

In the previous examples the imaging zone of the antenna was positioned in the homogeneous field zone by the detection of a signal from the antenna. An alternative to doing this is to have a defined relationship between the antenna and the subject support. This defined relationship can then be used to position the coil instead of measuring the signal from the antenna. For example in FIGS. 9, 10 and 11 various examples of coils 900, 1000, 124 are shown. These coils 900, 1000, 124 could alternatively be mounted at known locations on the subject support 120. The location of a scout scan or even a complete magnetic resonance image scan could then be determined by referencing or using the known location of the coil 900, 1000, 124. This is illustrated in FIGS. 12, 13 and 14.

Figure 12:
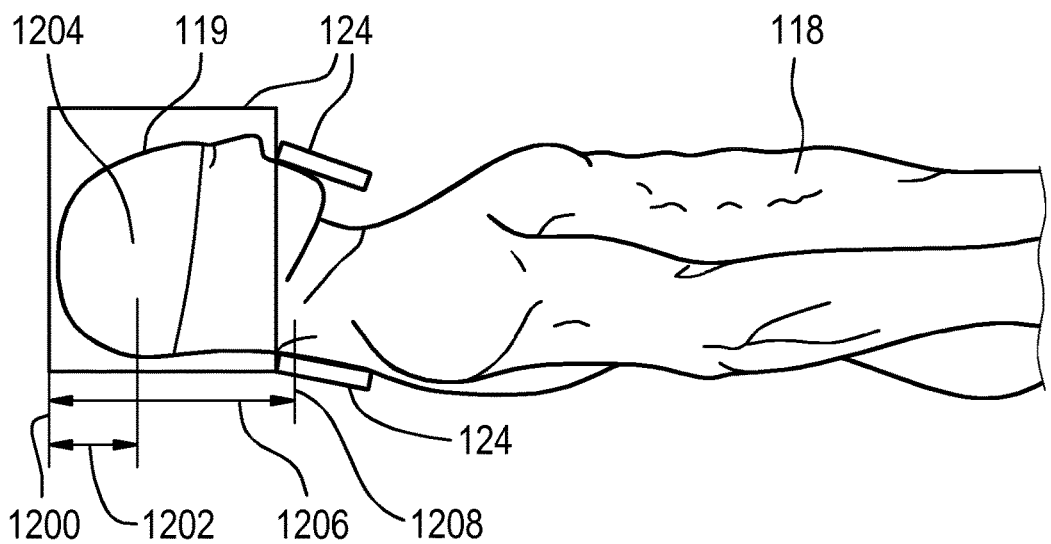
FIG. 12 illustrates the use of a coil is mounted to the subject support such that a coil reference location is known.

In the first example in FIG. 12 the coil 124 is mounted to the subject support such that a coil reference location 1200 is known. Having a knowledge of a subject's 118 particular anatomy or using an average anatomy for example the subject's weight and/or height anatomical locations relative to a reference point can be inferred. For instance a brain offset 1202 which gives a distance to a typical brain location 1204 could be used to set up a scan of the subject's brain 118. As another example a typical offset 1206 indicating a typical cervical spine location 1208 could be used to identify a cervical spine location 1208 to perform a magnetic resonance imaging scout or imaging clinical scan of the subject's 118 cervical spine.

In the example in FIG. 12 the coil 124 may also be used for imaging the brain and/or the cervical spine.

The targeted anatomy or the antenna may be brought to the isocenter or the predetermined location in a two-step approach:
1. Course positioning in such a way that a survey scan can be performed on which the operator can plan the following diagnostic scans or that SmartExam can be performed where the system recognizes a set of landmarks based on which the system proposes the planning of the diagnostic scans.
2. Fine positioning (if needed), based on the planning information from the survey or SmartExam.

The operator may prepare the patient (apply coil, headset, nurse call and/or physiology sensors), pushes a button to start automatic travel to scan plane (without using the light visor) and leaves the exam room. The system moves the targeted anatomy automatically to the isocenter based on the following techniques:

In a first technique, the table position can be derived from a previous scan session with the same patient, e.g. when the patient has been scanned before (follow-up scan).

In a second technique, some coils have a fixed position on the table top, such as the head coil or head/neck coil. When such a coil is connected and such an anatomy is selected, the tabletop can move towards the isocenter or a predetermined location. As a first order approach the coil goes to the isocenter.

However, the coil encloses multiple anatomies (e.g. brain, C-spine). It is worthwhile to be able to position on that targeted anatomy than simply position the coil in the isocenter. Therefore a coil reference location is defined. The coil reference location is an arbitrary location at the coil, in this example it is chosen at the end of the coil. There is a distance between this coil reference location and the typical location of the targeted anatomy, see FIG. 1. The offset of the typical anatomy with respect to the coil reference location can be derived from demographic data (pre-knowledge). The table will move into the scanner until the coil reference location, corrected with the typical offset for the targeted anatomy, hits the isocenter.

In a third technique, other anatomies (e.g. T-spine, cardiac) that are scanned with a coil which has no fixed location of the tabletop we can use the typical distances compared to the head, or better to say, compared to the base coil reference location. This is based on demographic data (pre-knowledge).

The table can move to more or less the right position for the targeted anatomy and perform the survey scan for planning or perform the SmartExam. The combination with patient characteristics such as age, weight and length would make the estimated distance from head to the targeted anatomy more accurate (cf. FIG. 13).

FIG. 13 shows an example where the coil reference location 1200 is simply used for positioning the subject 118. In this example a typical cardiac offset 1300 is used to identify a typical cardiac location 1302 in the subject 118. Again the subject's height and/or weight could be used to determine the cardiac offset 1300. The coil 124 could also be replaced by a receptacle on the surface of the subject support which receives the subject's head.

In case there is no coil present/connected with fixed position on the table, the following procedure can be used (this procedure is described for head first but can also be used for feet first):
a. The table is moved to a position where the head can be expected.
b. A scan is made at the location where the head is expected. For such a scan the body coil can be used as receive coil. A pattern recognition (e.g. scull shape at posterior side, nose, jaw) is used to determine the 'head center location' (see FIG. 14). This can be based on a low resolution single slice sagittal scan.
c. The typical offset to the targeted anatomy is derived from demographic data (pre-knowledge) and the table is moved to that location (if needed).
d. If needed alternative anatomical landmarks could be scanned, such as the shoulder or the diaphragm or by counting the vertebrae in the spine. In some cases another slice orientation would be needed.

In case of feet first a similar approach can be followed to detect the position of the feet, knee, hips and to have a typical offset from that anatomical point to the targeted anatomy.

When the examples in FIG. 12 or 13 are performed additional scout scans may also be performed as the subject is moving. FIG. 14 illustrates several scouts scans 1400 and their relation to the head center location 1402 using pattern recognition. For example, scout scans 1400 may be performed and used to identify the head center location 1402 more accurately.

In another technique, if needed this scanning is performed while the table is moving. An already known 'moving bed imaging technique' can be used or a single shot technique.

For further workflow optimization the operator can initiate the table or subject support movement and leave the exam room. Some magnetic resonance imaging systems have a RF door detection system or sensor. As soon as the operator closes the RF door, the door detection starts the scan (i.e. coil position detection). This is an additional workflow improvement.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 homogeneous field zone
109 center of homogeneous field zone
110 magnetic field gradient coils
112 magnetic field gradient coil power supply
114 body coil
116 transceiver
118 subject
119 head
120 subject support
122 mechanism
124 antenna
126 imaging zone
128 center of imaging zone
130 movement axis
132 computer system
134 hardware interface
136 processor
138 user interface
140 computer storage
142 computer memory
150 location pulse sequence
152 radio frequency signal
154 current location of coil
156 predetermined location
158 magnetic resonance planning data
160 magnetic resonance imaging pulse sequence
162 magnetic resonance data
164 magnetic resonance image
166 scout scan pulse sequence
168 scout magnetic resonance data
170 scout magnetic resonance image
172 anatomical landmark location
180 control module
182 magnetic resonance data processing module
184 image reconstruction module
186 image registration module
188 magnetic resonance planning data adjustment module
400 control the patient support to move the antenna and the portion of a subject from outside of the homogeneous field zone to within the homogeneous field zone along the movement axis
402 control the radio frequency system to repeatedly generate the radio frequency pulse
404 control the magnetic gradient field system to generate the gradient magnetic field during movement of the subject support only along the movement axis
406 control the radio frequency system to repeatedly measure the radio frequency signal from the portion of the subject using the antenna
408 determine a current location of the antenna or of the imaging zone using the radio frequency signal
410 control the patient support to decelerate and halt at a predetermined location within the homogeneous field zone using the current location.
500 Targeted anatomy is selected
502 Patient is prepared
504 Operator pushes "move" button
506 Operator walks to RF door
508 Patient moves into the scanner
510 RF door is closed
512 RF pulses are generated and MR signal received to determine the coil position
514 coil is in isocenter
516 Perform survey scan or planning scan or SmartExam
518 Additional table movements if needed for subsequent clinical scans.
600 pulse sequence
602 transmit pulse or RF pulse
604 switched z-gradient
606 received RF pulse or radio frequency signal
700 pulse sequence
702 constant gradient
704 free induction decay or radio frequency signal
800 pulse sequence
900 foot ankle coil
1000 breast coil
1200 coil reference location
1202 brain offset
1204 typical brain location
1206 typical cervical spine offset
1208 typical cervical spine location
1300 cardiac offset
1302 typical cardiac location
1400 location of scout scans
1402 head center location

The invention claimed is:

1. A magnetic resonance imaging system for imaging a portion of a subject comprising:
a magnet for generating a main magnetic field, wherein the main magnetic field has a homogeneous field zone;
an antenna with an imaging zone, wherein there is a fixed geometric relationship between the antenna and the portion of the subject when the subject is mounted in the imaging zone;
a radio frequency system for generating a radio frequency pulse, wherein the radio frequency system is further operable for measuring a radio frequency signal from the portion of the subject using the antenna;
a magnetic gradient field system for generating a gradient magnetic field;
a subject support for automatically moving the antenna and the portion of the subject from outside of the homogeneous field zone to within the homogeneous field zone along a movement axis;
a memory containing machine executable instructions;
a processor for controlling the magnetic resonance imaging system, wherein execution of the machine executable instructions causes the processor to:
control the subject support to move the antenna and the portion of the subject from outside of the homogeneous field zone to within the homogeneous field zone along the movement axis;
control the radio frequency system to repeatedly generate the radio frequency pulse;
control the magnetic gradient field system to generate the gradient magnetic field during movement of the subject support only along the movement axis;
control the radio frequency system to repeatedly measure the radio frequency signal from the portion of the subject using the antenna;

determine during movement of the subject support a current location of the antenna or of the imaging zone using the radio frequency signal; and control the subject support to decelerate and halt at a predetermined location within the homogeneous field zone using the current location.

2. The magnetic resonance imaging system of claim 1 wherein the gradient magnetic field along the movement axis is applied as a constant gradient magnetic field during movement of the subject support.

3. The magnetic resonance imaging system of claim 2, wherein execution of the machine executable instructions further causes the processor to control the magnetic gradient field system to increase the gradient magnetic field at a predetermined rate as the current location approaches the predetermined location.

4. The magnetic resonance imaging system of claim 1, wherein the radio frequency signal is a free induction decay that starts after the generation of the radio frequency pulse.

5. The magnetic resonance imaging system of claim 1, wherein the gradient magnetic field along the movement axis is repeatedly generated as a gradient magnetic field pulse during movement of the subject support.

6. The magnetic resonance imaging system of claim 5, wherein the gradient magnetic field pulse is generated after the radio frequency pulse is generated and before the measurement of the radio frequency signal.

7. The magnetic resonance imaging system of claim 1, wherein the memory further contains magnetic resonance planning data descriptive of a magnetic resonance imaging scan geometry, wherein execution of the machine executable instructions further causes the processor to:
control the magnetic resonance imaging system to acquire imaging magnetic resonance data defined by the magnetic resonance imaging scan geometry; and
reconstruct a magnetic resonance imaging from the imaging magnetic resonance data.

8. The magnetic resonance imaging system of claim 7, wherein the memory further contains scout scan pulse sequence instructions, wherein the magnetic resonance planning data is descriptive of the magnetic resonance imaging scan geometry relative to anatomical landmarks of the subject, wherein the memory further contains imaging pulse sequence instructions,
wherein execution of the scout scan pulse sequence instructions further causes the processor to:
control the magnetic resonance imaging system to acquire scout magnetic resonance data using the scout scan pulse sequence instructions;
reconstruct the scout magnetic resonance data into a scout magnetic resonance image; and
identify landmark location data using by identifying the anatomical landmarks in the scout magnetic resonance image.

9. The magnetic resonance imaging system of claim 8, wherein execution of the scout scan pulse sequence instructions further causes the processor to modify the imaging pulse sequence instructions using the landmark location data and the magnetic resonance planning data to adjust the scan geometry.

10. The magnetic resonance imaging system of claim 8, wherein execution of the scout scan pulse sequence instructions further cause the processor to:
calculate a corrective movement of the subject support by using the landmark location data and the magnetic resonance planning data; and control the subject support to move by a determined distance.

11. The magnetic resonance imaging system of claim 1, wherein the current location indicates a location of the imaging zone.

12. The magnetic resonance imaging system of claim 1, wherein the radio frequency pulse is a non-selective pulse.

13. The magnetic resonance imaging system of claim 1, wherein execution of the machine executable instructions causes the processor to generate a radio frequency pulse at an increased rate and/or increased gradient magnetic field as the current location approaches the predetermined location.

14. A method of operating a magnetic resonance imaging system for imaging a portion of a subject, wherein the magnetic resonance imaging system comprises:
a magnet for generating a main magnetic field, wherein the main magnetic field has a homogeneous field zone;
an antenna with an imaging zone, wherein there is a fixed geometric relationship between the antenna and the portion of the subject when the subject is mounted in the imaging zone;
a radio frequency system for generating a radio frequency pulse, wherein the radio frequency system is further operable for measuring a radio frequency signal from the portion of the subject using the antenna;
a magnetic gradient field system for generating a gradient magnetic field;
a subject support for automatically moving the antenna and the portion of the subject from outside of the homogeneous field zone to within the homogeneous field zone along a movement axis;
wherein the method comprises the steps of:
controlling the subject support to move the antenna and the portion of a subject from outside of the homogeneous field zone to within the homogeneous field zone along the movement axis;
controlling the radio frequency system to repeatedly generate the radio frequency pulse;
controlling the magnetic gradient field system to generate the gradient magnetic field during movement of the subject support only along the movement axis;
controlling the radio frequency system to repeatedly measure the radio frequency signal from the portion of the subject using the antenna;
determining during movement of the subject support a current location of the antenna or of the imaging zone using the radio frequency signal; and
controlling the subject support to decelerate and halt at a predetermined location within the homogeneous field zone using the current location.

15. A non-transitory computer-readable storage medium that stores machine executable instructions for execution by a processor controlling a magnetic resonance imaging system for imaging a portion of a subject, wherein the magnetic resonance imaging system comprises:
a magnet for generating a main magnetic field, wherein the main magnetic field has a homogeneous field zone;
an antenna with an imaging zone, wherein there is a fixed geometric relationship between the antenna and the portion of the subject when the subject is mounted in the imaging zone;
a radio frequency system for generating a radio frequency pulse, wherein the radio frequency system is further operable for measuring a radio frequency signal from the portion of the subject using the antenna;
a magnetic gradient field system for generating a gradient magnetic field;

a subject support for automatically moving the antenna and the portion of the subject from outside of the homogeneous field zone to within the homogeneous field zone along a movement axis;

wherein execution of the machine executable instructions causes the processor to:

control the subject support to move the antenna and the portion of a subject from outside of the homogeneous field zone to within the homogeneous field zone along the movement axis;

control the radio frequency system to repeatedly generate the radio frequency pulse;

control the magnetic gradient field system to generate the gradient magnetic field during movement of the subject support only along the movement axis;

control the radio frequency system to repeatedly measure the radio frequency signal from the portion of the subject using the antenna;

determine during movement of the support a current location of the antenna or of the imaging zone using the radio frequency signal; and control the subject support to decelerate and halt at a predetermined location within the homogeneous field zone using the current location.

16. The non-transitory computer-readable storage medium of claim 15, wherein non-transitory computer-readable storage medium further comprises magnetic resonance planning data descriptive of a magnetic resonance imaging scan geometry, and execution of the machine executable instructions further causes the processor to: memory further contains magnetic resonance planning data descriptive of a magnetic resonance imaging scan geometry control the magnetic resonance imaging system to acquire imaging magnetic resonance data defined by the magnetic resonance imaging scan geometry; and reconstruct a magnetic resonance imaging from the imaging magnetic resonance data.

17. The non-transitory computer-readable storage medium of claim 16, wherein non-transitory computer-readable storage medium further contains scout scan pulse sequence instructions, wherein the magnetic resonance planning data is descriptive of the magnetic resonance imaging scan geometry relative to anatomical landmarks of the subject, wherein the non-transitory computer-readable storage medium further contains imaging pulse sequence instructions, wherein execution of the machine executable instructions further causes the processor to:

control the magnetic resonance imaging system to acquire scout magnetic resonance data using the scout scan pulse sequence instructions;

reconstruct the scout magnetic resonance data into a scout magnetic resonance image; and identify landmark location data using by identifying the anatomical landmarks in the scout magnetic resonance image.

18. The non-transitory computer-readable storage medium of claim 17, wherein execution of the machine executable instructions further causes the processor to modify the imaging pulse sequence instructions using the landmark location data and the magnetic resonance planning data to adjust the scan geometry.

19. The non-transitory computer-readable storage medium of claim 17, wherein execution of the machine executable instructions further cause the processor to:

calculate a corrective movement of the subject support by using the landmark location data and the magnetic resonance planning data; and control the subject support to move by a determined distance.

20. The non-transitory computer-readable storage medium of claim 15, wherein execution of the machine executable instructions causes the processor to generate a radio frequency pulse at an increased rate and/or increased gradient magnetic field as the current location approaches the predetermined location.

* * * * *